US012797574B2

(12) United States Patent

Okano et al.

(10) Patent No.: US 12,797,574 B2

(45) Date of Patent: Nov. 17, 2026

(54) ION GENERATOR AND METHOD FOR SUPPRESSING DROWSINESS

(71) Applicant: SHARP KABUSHIKI KAISHA, Sakai City (JP)

(72) Inventors: Hiroaki Okano, Sakai City (JP); Hirokazu Funamori, Sakai City (JP)

(73) Assignee: SHARP KABUSHIKI KAISHA, Sakai City (JP)

(*) Notice: Subject to any disclaimer, the term of this patent is extended or adjusted under 35 U.S.C. 154(b) by 565 days.

(21) Appl. No.: 18/279,203

(22) PCT Filed: Feb. 18, 2022

(86) PCT No.: PCT/JP2022/006637

§ 371 (c)(1),
(2) Date: Aug. 28, 2023

(87) PCT Pub. No.: WO2022/185953

PCT Pub. Date: Sep. 9, 2022

(65) Prior Publication Data

US 2024/0165369 A1 May 23, 2024

(30) Foreign Application Priority Data

Mar. 1, 2021 (JP) ................................. 2021-032115

(51) Int. Cl.

*A61M 21/00* (2006.01)
*A61L 9/22* (2006.01)
*F24F 8/30* (2021.01)
*H01T 23/00* (2006.01)

(52) U.S. Cl.

CPC ............... *A61M 21/00* (2013.01); *A61L 9/22* (2013.01); *F24F 8/30* (2021.01); *H01T 23/00* (2013.01); *A61M 2021/0077* (2013.01); *A61M 2021/0083* (2013.01)

(58) Field of Classification Search

CPC . A61M 21/00; A61M 2021/0083; A61L 9/22; F24F 8/30; F24F 11/76; F24F 11/80; H01T 23/00; A61B 5/00; A61B 5/4809; A61B 5/18; G08G 1/16

USPC .................................................. 361/232–233

See application file for complete search history.

(56) References Cited

U.S. PATENT DOCUMENTS

2016/0001781 A1* 1/2016 Fung ...................... G06V 10/82 701/36
2016/0334141 A1* 11/2016 Shifferaw ................. F03G 7/04
2020/0082700 A1* 3/2020 Shikii ....................... A61B 5/16
2020/0240670 A1* 7/2020 Kitagawa ................. F24F 11/30

FOREIGN PATENT DOCUMENTS

JP H08-290726 A 11/1996
JP 2005-170325 A 6/2005
JP 2007-265377 A 10/2007
JP 2011-065561 A 3/2011

* cited by examiner

*Primary Examiner* — Danny Nguyen

(74) *Attorney, Agent, or Firm* — ScienBiziP, P.C.

(57) ABSTRACT

An ion generator is configured to emit, in accordance with a state of a worker in a workspace (S2), air containing ions into the workspace (S3).

5 Claims, 5 Drawing Sheets

| DEGREE OF DROWSINESS | ION EMISSION LEVEL |
|---|---|
| DEGREE OF DROWSINESS 0 | ION EMISSION LEVEL 0 |
| DEGREE OF DROWSINESS 1 | ION EMISSION LEVEL 1 |
| DEGREE OF DROWSINESS 2 | ION EMISSION LEVEL 2 |
| DEGREE OF DROWSINESS 3 | ION EMISSION LEVEL 3 |

| | GROUP A EVALUATION VALUE | GROUP B EVALUATION VALUE | RATIO (GROUP A / GROUP B) |
|---|---|---|---|
| POSITIVE FEELING | 11145 | 9782 | 1.14 |
| DRIVING RESPONSE | 8154 | 6425 | 1.27 |

ION GENERATOR AND METHOD FOR SUPPRESSING DROWSINESS

TECHNICAL FIELD

The present invention relates to an ion generator and a method for suppressing drowsiness.

BACKGROUND ART

Various techniques for preventing drowsy driving have been proposed. For example, PTL 1 discloses a drowsiness warning device for preventing drowsy driving. The drowsiness warning device estimates driver alertness in accordance with an amount of time that the eyes of the driver stay closed. Further, the drowsiness warning device determines, by a state of the vehicle, whether it is acceptable for the driver to doze off. The drowsiness warning device outputs a warning in accordance with the estimation of alertness and the determination result of the state of the vehicle.

CITATION LIST

Patent Literature

PTL 1: JP 08-290726 A

SUMMARY OF INVENTION

Technical Problem

Drowsiness is not only likely to be induced when driving a vehicle, but also when performing simple tasks or light work in factories, offices, or the like, and readily results in a reduction in work efficiency. In the case of the drowsiness warning device described in PTL 1, even if the drowsiness of the worker is temporarily reduced by the output of the warning, there is a high possibility that the drowsiness will be induced again as time passes. Further, even if the drowsiness is temporary, if the worker is not actively engaged in the work, work efficiency decreases.

The present invention has been made in view of the problems described above, and an object thereof is to provide a technique capable of suppressing drowsiness of a worker and improving work efficiency.

Solution to Problem

An ion generator according to the present invention is configured to emit air containing ions into a workspace in accordance with a state of a worker in the workspace.

Further, a method for suppressing drowsiness according to the present invention includes using the ion generator described above to suppress drowsiness of the worker.

Advantageous Effects of Invention

According to the ion generator and the method for suppressing drowsiness of the present invention, it is possible to suppress drowsiness of a worker and improve work efficiency.

DESCRIPTION OF EMBODIMENTS

Figures 1, 2:
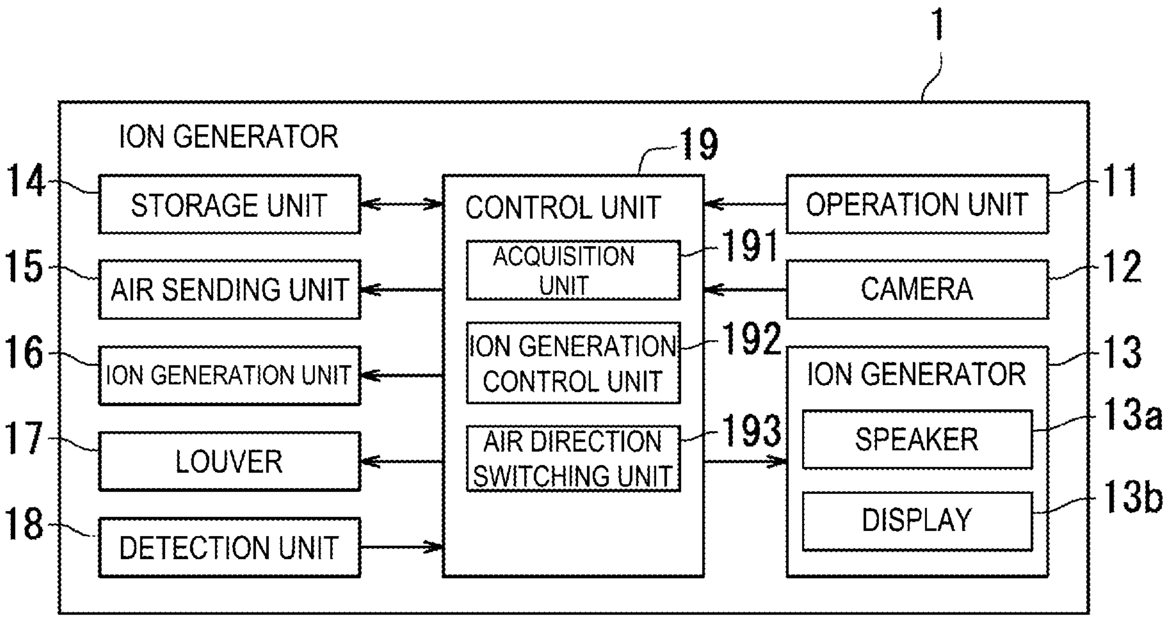
FIG. 1 is a block diagram illustrating an overall configuration of an ion generator according to an embodiment.
FIG. 2 is a diagram illustrating an example of ion emission control information.

Embodiments of the present invention will be described hereinafter with reference to the accompanying drawings. Note that, in the drawings, the same or equivalent components are denoted by the same reference numerals and signs, and description thereof will not be repeated.

An ion generator according to the embodiment is installed in a workspace and emits air containing ions into the workspace in accordance with a state of a worker who performs work in the workspace. Hereinafter, a configuration of the ion generator according to the embodiment will be specifically described.

Configuration

FIG. 1 is a block diagram illustrating a configuration example of an ion generator 1 according to the embodiment. As illustrated in FIG. 1, the ion generator 1 includes an operation unit 11, a camera 12, a notification unit 13, a storage unit 14, an air sending unit 15, an ion generation unit 16, a louver 17, a detection unit 18, and a control unit 19.

The operation unit 11 includes operation buttons such as a power button. The operation unit 11 outputs an operation signal indicating that the operation button was operated to the control unit 19.

The camera 12 outputs imaging data obtained by imaging a subject to the control unit 19. Note that the camera 12 need only be disposed so as to capture at least an upper body including a head of the worker. The camera 12 may be externally attached to the ion generator 1 or may be incorporated into the ion generator 1.

The notification unit 13 includes a speaker 13*a* and a display 13*b*. The speaker 13*a* outputs sound under the control of the control unit 19. The display 13*b* is provided at a position in the ion generator 1 that is visible by the worker, for example. The display 13*b* displays an image under the control of the control unit 19.

The storage unit 14 includes a nonvolatile storage medium such as a flash memory or a hard disk. The storage unit 14 stores ion emission control information used for ion generation processing, information to be provided in a notification from the notification unit 13, and the like.

FIG. 2 is a diagram illustrating an example of the ion emission control information. As illustrated in FIG. 2, in the ion emission control information, a plurality of degrees of drowsiness and a plurality of ion emission levels are associated with one other. The degree of drowsiness is an indicator indicating the degree of drowsiness of the worker. The ion emission level is an indicator indicating the amount of ions emitted per unit time. In the embodiment, a smaller numerical value of the degree of drowsiness indicates a state of less drowsiness, that is, a more alert state. A smaller numerical value of the ion emission level indicates a smaller emission amount of the ions per unit time.

Figure 3:
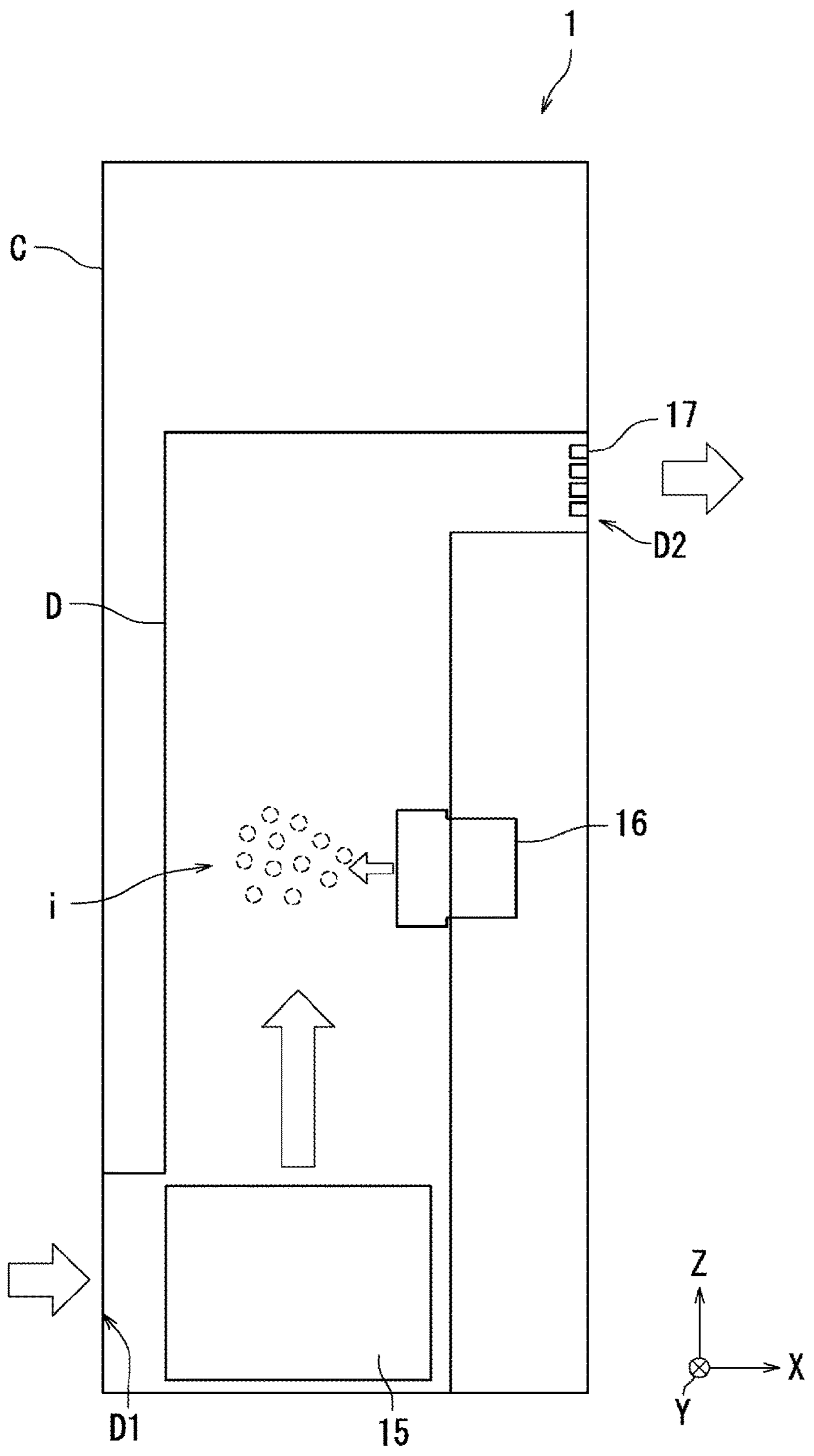
FIG. 3 is an overall cross-sectional view of the ion generator.

Referring back to FIG. 1, the air sending unit 15, the ion generation unit 16, and the louver 17 will be described with reference to FIG. 3. FIG. 3 is an overall cross-sectional view of the ion generator 1. As illustrated in FIG. 3, the ion generator 1 includes a case C and a duct D provided in the case C. The duct D connects an opening D1 formed in a surface of the case C on a negative X-axis direction side and an opening D2 formed in a surface of the case C on a positive X-axis direction side. Hereinafter, the opening D1 side of the duct D may be referred to as upstream, and the opening D2 side may be referred to as downstream.

The air sending unit 15 is disposed at or near the opening D1. The air sending unit 15 includes a fan and a motor (both of which are not illustrated). Under the control of the control unit 19, the air sending unit 15 drives the motor to rotate the fan, thereby taking in external air from the opening D1 of the ion generator 1 and generating an airflow. The motor rotates at a number of revolutions (RPM) corresponding to the ion emission level instructed by the control unit 19. A smaller numerical value of the ion emission level indicates a smaller number of revolutions of the motor and a smaller volume of air sent. In the embodiment, the number of revolutions of the motor for an ion emission level of "0" is 0 (RPM) and, in this case, the driving of the motor is stopped.

The ion generation unit 16 is disposed downstream of the air sending unit 15. The ion generation unit 16 generates ions i (positive ions and negative ions) by corona discharge, for example. The ions i generated are emitted into the inside of the duct D. More specifically, the ion generation unit 16 includes a pair of discharge electrodes disposed spaced apart from each other and a voltage generation circuit (both of which are not illustrated). The discharge electrodes include, for example, a brush-like electrode formed by bundling a plurality of conductors. The voltage generation circuit applies, under the control of the control unit 19, a predetermined voltage of negative polarity to one of the discharge electrodes and a predetermined voltage of positive polarity to the other of the discharge electrodes. Negative ions are generated at or near a tip of the discharge electrode to which the predetermined voltage of negative polarity is applied, and positive ions are generated at or near a tip of the discharge electrode to which the predetermined voltage of positive polarity is applied. An amount of ions i (positive ions and negative ions) emitted to the outside of the duct D per unit time increases as the volume of air sent from upstream increases. Note that a shape of the discharge electrodes is not limited to a brush shape, and may be a needle shape, a rod shape, a planar shape, or the like.

In the embodiment, the positive ions are cluster ions in which a plurality of water molecules are clustered around a hydrogen ion ($H^+$), and are expressed by $H^+(H_2O)_m$, where m is any integer of zero or greater. Further, the negative ions are cluster ions in which a plurality of water molecules are clustered around an oxygen ion ($O_2^-$), and are expressed by $O_2^-(H_2O)_n$, where n is any integer of zero or greater. Such positive ions and negative ions, when emitted into the air, surround airborne mold bacteria and viruses and chemically react with each other on surfaces thereof. At this time, hydroxyl radicals (·OH), which are active species, are generated, and the mold bacteria, viruses, and the like are removed by the action of the hydroxyl radicals.

The louver 17 is provided at the opening D2, that is, at an outlet of the airflow containing ions. In FIG. 3, the worker (not illustrated) is positioned on the positive X-axis direction side of the ion generator 1, that is, in the direction in which the airflow containing ions is blown out. The louver 17 includes a plurality of blades capable of adjusting the direction in which the airflow is blown to the outside, that is, an air direction. The air direction based on the plurality of blades is controlled by the control unit 19.

Referring back to FIG. 1, the detection unit 18 includes, for example, a motion sensor that uses infrared rays. The detection unit 18 is provided on the opening D2 side of the case C of the ion generator 1 illustrated in FIG. 3, for example. The detection unit 18 detects infrared rays within a predetermined detection range to detect the position (direction) of the worker, and outputs the detection result to the control unit 19.

The control unit 19 includes a central processing unit (CPU) and memory (read-only memory (ROM) and random access memory (RAM)). The CPU executes a control program stored in the ROM, thereby causing the control unit 19 to function as an acquisition unit 191, an ion generation control unit 192, and an air direction switching unit 193.

The acquisition unit 191 sequentially acquires imaging data input from the camera 12 and identifies at regular time intervals, as worker information indicating the state of the worker, information indicating a degree of drowsiness of the worker, on the basis of the imaging data.

As a method for identifying the degree of drowsiness of the worker, identification may be made by using a trained program that uses sample face image data prepared in advance for each degree of drowsiness 0 to 3 (FIG. 2) as teaching data for learning, and outputs any one of the degrees of drowsiness 0 to 3 from the face image data inputted. The sample face image data may include face image data of the worker and face image data of a person other than the worker.

Note that the trained program may be stored in the storage unit 14 of the ion generator 1 or may be stored in an external device. For example, in a case in which the trained program is stored in an external server, the ion generator 1 includes a communication interface for establishing a communication connection with the external server. The acquisition unit 191 transmits the acquired imaging data to the external server via the communication interface and acquires information indicating the degree of drowsiness from the external server at regular time intervals.

The ion generation control unit 192 identifies the ion emission level corresponding to the degree of drowsiness identified by the acquisition unit 191 in the ion emission control information stored in the storage unit 14. Then, the ion generation control unit 192 causes the ion generation unit 16 to generate ions, controls the air sending unit 15 on the basis of the identified ion emission level, and controls the emission amount of ions per unit time emitted from the duct P (FIG. 3) to the outside. In the embodiment, the ion generation control unit 192 controls the emission amount of ions per unit time by adjusting the air volume per unit time sent downstream from the air sending unit 15, that is, the airflow rate. Specifically, the ion generation control unit 192 transmits a signal indicating a predetermined number of revolutions corresponding to the ion emission level to the motor of the air sending unit 15. That is, as the numerical value of the ion emission level increases, a signal indicating a larger number of revolutions is sent to the air sending unit 15, increasing the airflow rate.

The air direction switching unit 193 changes the direction of the blades of the louver 17 on the basis of the detection result output from the detection unit 18. That is, the direction of the blades of the louver 17 is changed so that the air containing ions is blown in the direction in which the worker is present indicated by the detection result.

Operation

Figure 4:
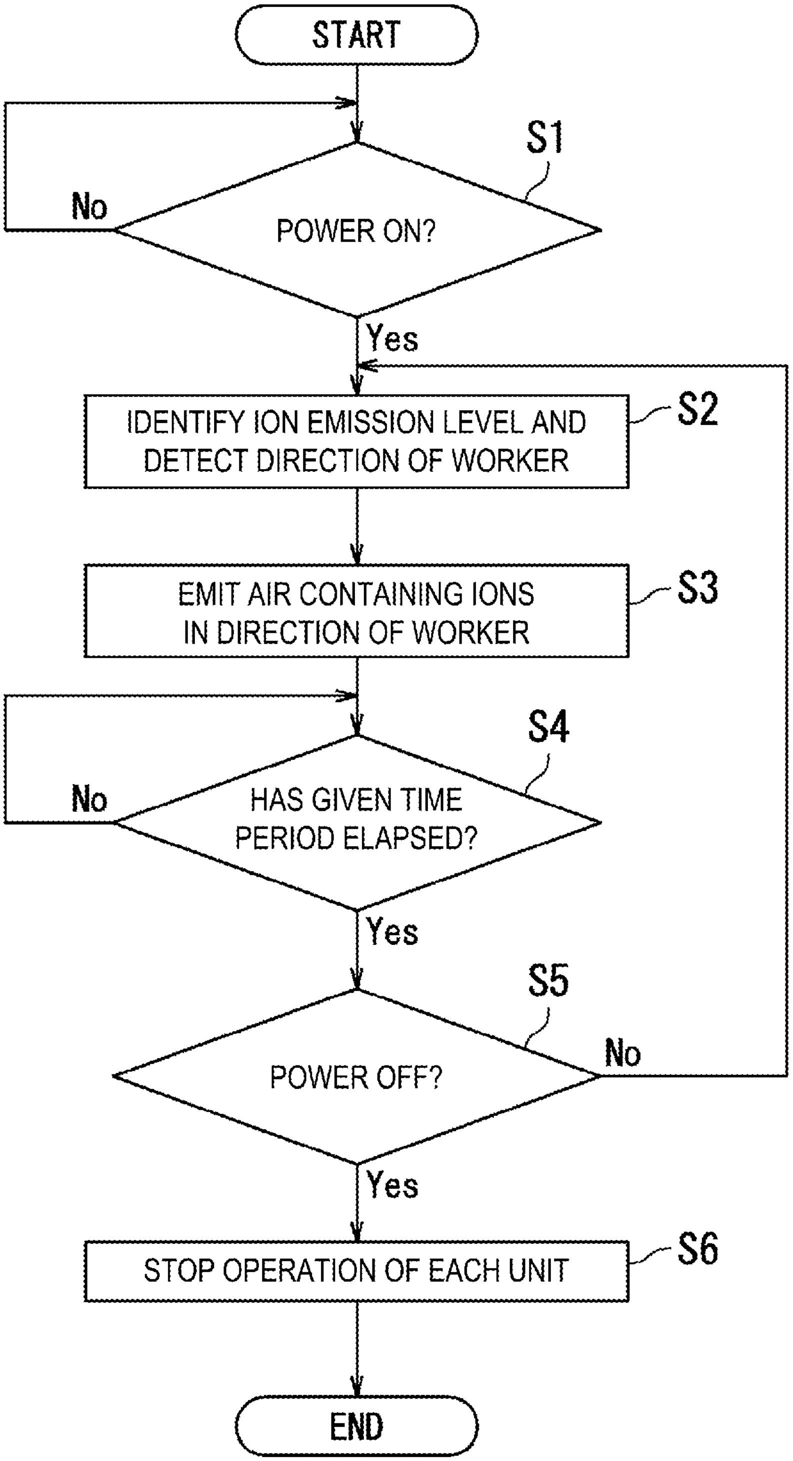
FIG. 4 is an operation flowchart illustrating an example of operation of the ion generator according to the embodiment.

Next, operation of the ion generator 1 will be described with reference to FIG. 4. FIG. 4 is a flowchart illustrating an example of the operation of the ion generator 1 according to the embodiment. Hereinafter, the operation of the ion generator 1 will be described with reference to FIGS. 1 to 3.

In a case in which an operation for turning on the power supply of the ion generator 1 is performed via the operation unit 11 (step S1: Yes), the ion generator 1 identifies the ion emission level and detects the direction in which the worker is present relative to the ion generator 1 (step S2).

Specifically, the ion generator 1, in the acquisition unit 191, causes the camera 12 to start imaging, acquires the imaging data from the camera 12, and stores the imaging data in the memory. The acquisition unit 191 identifies the degree of drowsiness of the worker in the imaging data acquired from the camera 12 by using a predetermined trained program. Then, the ion generator 1, in the ion generation control unit 192, refers to the ion emission control information (FIG. 2) stored in the storage unit 14 and identifies the ion emission level corresponding to the identified degree of drowsiness. Further, the ion generator 1 detects, by the detection unit 18, infrared rays within a predetermined detection range to detect the direction in which the worker is present.

The ion generator 1 emits, on the basis of the identified ion emission level and the detected direction in which the worker is present, the air containing ions in the direction in which the worker is present (step S3). Specifically, the ion generation control unit 192 causes the ion generation unit 16 to generate ions. Further, the ion generation control unit 192 rotates the motor of the air sending unit 15 at a predetermined number of revolutions corresponding to the ion emission level to generate an airflow in the duct P. The air direction switching unit 193 changes the direction of the blades of the louver 17 on the basis of the detection result of the detection unit 18 indicating the direction of the worker. As a result, the air containing ions is blown in the direction of the worker by the air being sent from the air sending unit 15.

The ion generator 1 continues the process of step S3 until a given time period elapses (step S4: No). Then, after the given time period elapses (step S4: Yes), the ion generator 1 repeats the processes of steps S2 to S4 until an operation of turning off the power supply is performed via the operation unit 11 (step S5: No). That is, until the power supply is turned off, the ion generator 1, at regular time intervals, identifies the ion emission level corresponding to the degree of drowsiness of the worker, and emits air containing ions at the emission amount of ions per unit time corresponding to the ion emission level.

When an operation for turning off the power is performed via the operation unit 11 (step S5: Yes), the ion generator 1 stops the operation of each unit (step S6).

Example of Use of Ion Generator 1

The workspace in which the ion generator 1 is installed may be a room or a moving space such as a vehicle. Further, the work may be light work, such as flow work or monitoring work in a factory, a driving operation of a vehicle, or the like. For example, in a case of being mounted on a vehicle, the ion generator 1 emits air containing ions toward a driver (worker) at an ion emission level corresponding to the degree of drowsiness of the driver. With the air containing ions being emitted, an effect of suppressing the drowsiness of the driver and improving a driving operability of the driver can be expected.

Hereinafter, experiment results verifying that the emission of air containing ions contributes to the suppression of drowsiness will be described.

Experiment Method

In the experiment, whether there is a difference in the degrees of drowsiness of drivers between a case in which ions are not generated and only air is emitted toward a driver during travel (hereinafter referred to as "air only") and a case in which air containing a predetermined amount of ions is emitted toward a driver during travel (hereinafter referred to as "with ions") was verified. More specifically, brain waves during travel were measured for each of the subjects of group A traveling with ions and the subjects of group B traveling with air only, and the degrees of drowsiness were evaluated on the basis of the measurement results. There were 13 subjects in each of the groups A and B in this experiment, and both groups A and B traveled on the same route. Further, in the experiment, an ion generator capable of switching between air only and with ions was used. The ion generator is, for example, a small-sized ion generator that can be disposed in a cup holder provided in a vehicle. The small-sized ion generator is supplied with electric power from an external power source such as a battery built into the device, a portable battery, or a cigarette lighter socket mounted in the vehicle. A Kansei Module Logger (manufactured by Littlesoftware Inc.) is used to measure the degree of drowsiness, and a value indicating the degree of drowsiness is output from the Kansei Module Logger on the basis of an output value of an electroencephalograph mounted on the head of the subject.

Figure 5:
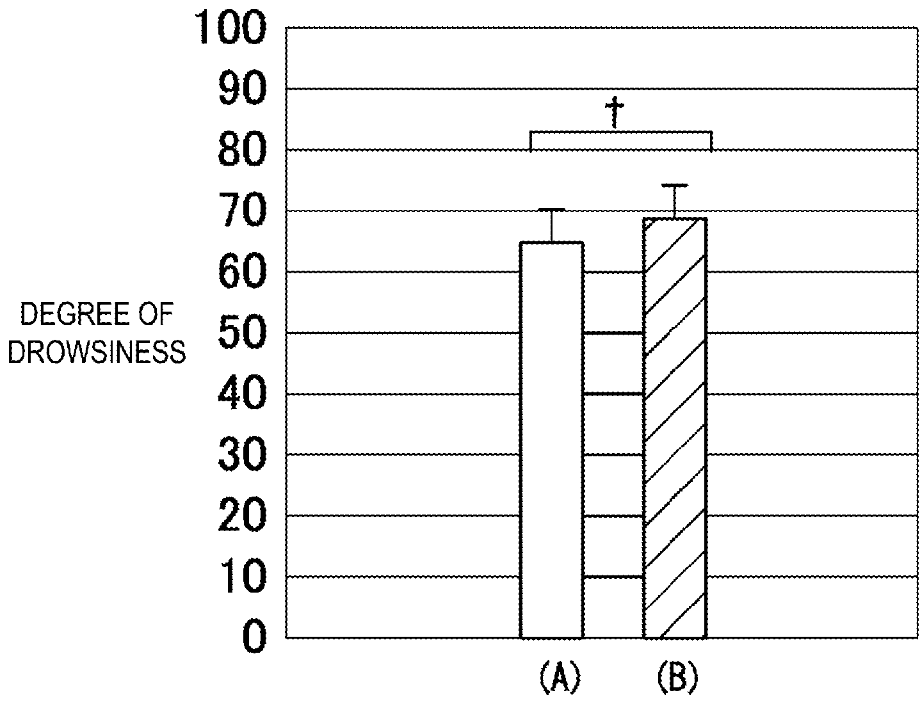
FIG. 5 is a graph showing a distribution of degrees of drowsiness obtained in an experiment.

FIG. 5 is a graph showing a distribution of the degrees of drowsiness of group A and group B obtained in the experiment. In FIG. 5, a higher numerical value of the degree of drowsiness indicates more drowsiness. As shown in FIG. 5, the degree of drowsiness of group A is lower than that of group B. Further, as a result of performing a t-test on group A and group B and calculating a p-value, the p-value related to the degree of drowsiness was 0.059. Therefore, group A (traveling with ions) has a more significant trend than group B (traveling with air only), and the drowsiness of the driver is regarded as readily suppressed by the emission of air containing a predetermined amount of ions.

Figures 6A, 6B:
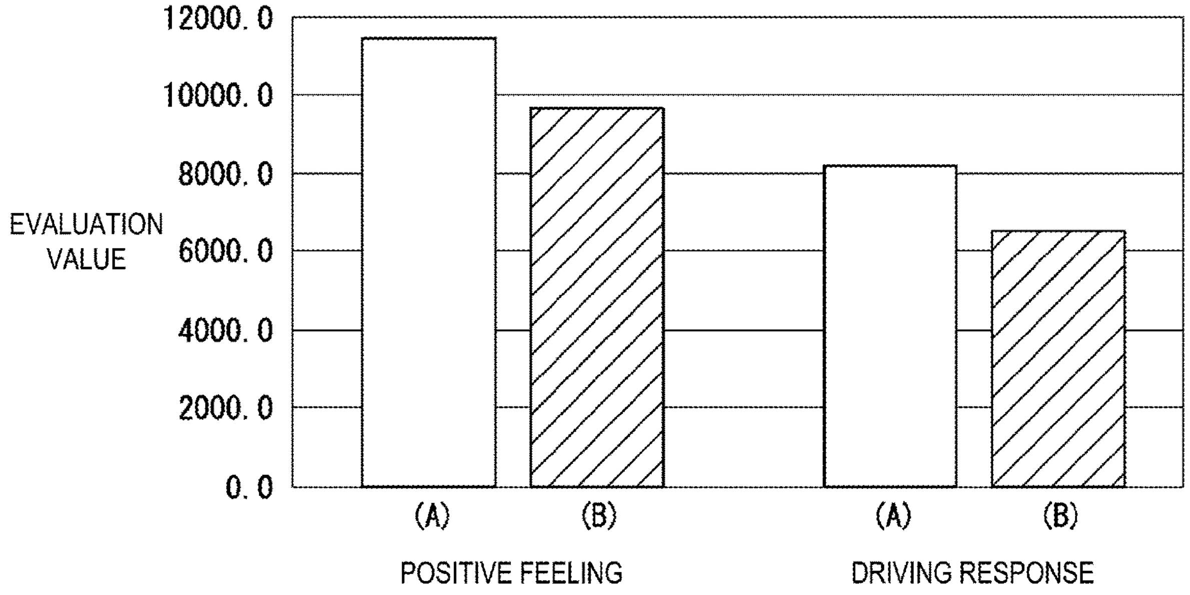
FIG. 6A is a graph showing evaluation results of positive feeling and driving response of group A and group B obtained in the experiment.
FIG. 6B is a table showing evaluation values and ratios of positive feeling and driving response of group A and group B obtained in the experiment.

Further. FIG. 6A is a graph showing the evaluation results of positive feeling and driving response of group A and group B obtained in the experiment, and FIG. 6B is a table showing the evaluation values and the ratios of positive feeling and driving response of group A and group B obtained in the experiment.

Each evaluation value of group A and group B in FIG. 6B is a result obtained by calculating each evaluation value of positive feeling and driving response of each driver on the basis of the result of analyzing the frequency of the brain waves of each driver during travel, and calculating the averages of the respective evaluation values of positive feeling and driving response of group A and group B.

The evaluation value representing positive feeling indicates how positive the driver is with respect to road conditions (traffic jam, curves, cut-ins, and the like) during driving, and a higher evaluation value indicates a more positive state. Further, the evaluation value representing the driving response indicates whether the driver can immediately respond to road conditions, and a higher evaluation value indicates a faster ability to respond to road conditions.

As shown in FIGS. 6A and 6B, the evaluation values of both positive feeling and driving response are higher in group A than in group B. Specifically, as shown in FIG. 6B, the evaluation value of positive feeling of group A is approximately 1.14 times that of group B, and the evaluation value of driving response of group A is approximately 1.27 times that of group B. The brain waves obtained in the experiment are related to drowsiness and alertness. Accordingly, the drivers of group A are regarded as having improved positivity with respect to driving and improved driving responsiveness due to the emission of the air containing ions.

The embodiments of the present invention have been described above with reference to the accompanying drawings. However, the present invention is not limited to the embodiments described above, and the present invention can be implemented in various modes without departing from the gist thereof. Further, various inventions can be formed by appropriately combining a plurality of components disclosed in the embodiments described above. For example, some components may be removed from all of the components described in the embodiments. Furthermore, the components across different embodiments may be appropriately combined. For ease of understanding, the drawings schematically illustrate each component as a main constituent, and the thickness, length, number, spacing, and the like of each component illustrated are different from the actual thickness, length, number, and spacing for convenience of drawing preparation. Further, the speed, material, shape, dimensions, and the like of each component illustrated in the embodiments described above are one example and are not particularly limited, and various modifications can be made within a range that does not substantially deviate from the configuration of the present invention.

MODIFIED EXAMPLES (1) In the ion generator 1, the method of adjusting the emission amount of ions per unit time in accordance with the degree of drowsiness is not limited to adjustment of the airflow rate generated by the air sending unit 15. For example, the ion generation control unit 192 may adjust the voltage level applied to the discharge electrodes from the voltage circuit in the ion generation unit 16 to change the emission amount of ions generated from the ion generation unit 16. Alternatively, the ion generation control unit 192 may cause the air sending unit 15 to intermittently generate an airflow having a constant airflow rate so that the emission amount of ions per unit time is in accordance with the degree of drowsiness. Alternatively, the emission amount of ions per unit time generated from the ion generation unit 16 may be changed by changing a distance between the pair of discharge electrodes in the ion generation unit 16.

(2) The degree of drowsiness of the worker may be identified as follows. For example, in the ion generator 1, a physical quantity indicating a change in at least one of a change in a facial expression of the worker, the movement of the worker, and biological information of the worker may be acquired, and the degree of drowsiness may be identified on the basis of the acquired physical quantity. The change in the facial expression of the worker may include, for example, a change in a number of blinks or in an iris size. The change in the movement of the worker may include a change in a position or an angle of the head of the worker, a change in a position of a hand of the worker, or the like. Further, the biological state of the worker may include at least one of a brain wave, a heartbeat, a pulse, and the like of the worker.

(3) The worker information may be other than the degree of drowsiness of the worker. For example, in the case of packing work for packing articles into a box, a number of packing tasks per unit time may be used as the worker information. Further, for example, in a case in which a driving operation is the work, a contact state with an object touched by the worker for performing the work, such as presence or absence of contact with a steering wheel or a contact time, may be set as the worker information. In short, the worker information may be a physical quantity indicating at least one of a physical state of the worker when the worker is performing the work and a state of the work being performed by the worker. For example, in a case in which a driving operation is the work, the ion generator 1 may increase the emission amount of ions per unit time when a state in which the driver (worker) is not in contact with the steering wheel continues for a given period of time or longer. That is, when the state of the work of the worker does not satisfy a predetermined condition, the ion generator 1 may increase the emission amount of ions per unit time.

(4) The worker information may be acquired from an external device provided outside the ion generator 1. In this case, the ion generator 1 includes a communication function for establishing a wired or wireless communication connection with the external device. The external device may be a server device connected to an Internet network. Further, in a case in which the ion generator 1 is mounted on a vehicle, the external device may be a computer device such as an electronic control unit (ECU) provided in the vehicle.

(5) In the ion generator 1, when the state of the worker changes to an alert state such as when the degree of drowsiness of the worker decreases or when the worker grips the steering wheel, the emission amount of ions per unit time may be reduced or the emission of ions may be stopped.

(6) In the ion generator 1, when the ion emission level is changed in accordance with a change in the degree of drowsiness of the worker, a notification of information indicating that the ion emission level is changed may be provided from the notification unit 13. For example, when the degree of drowsiness of the worker becomes high and the ion emission level is increased, notification of the changed ion emission level is provided so that the worker can recognize the state of drowsiness. Further, in the ion generator 1, when the ion emission level is changed, a notification of information indicating the state of the worker, such as the degree of drowsiness or the movement of the worker, may be provided from the notification unit 13.

(7) The ion generator 1 may be incorporated in an air conditioner or an air purifier installed in the workspace.

(8) Although the ion generator 1 described above emits air containing positive ions and negative ions to the outside according to the state of the worker, the ion generator 1 may generate negative ions using a known method (corona discharge. Lenard effect, photoelectric effect, or the like) and emit air containing negative ions to the outside.

INDUSTRIAL APPLICABILITY

The present invention can be utilized in factories, offices, vehicles, and the like.

REFERENCE SIGNS LIST

1 Ion generator
12 Camera

13 Notification unit
15 Air sending unit
16 Ion generation unit
17 Louver
18 Detection unit
191 Acquisition unit
192 Ion generation control unit
193 Air direction switching unit

The invention claimed is:

1. An ion generator configured to emit air containing ions into a workspace in accordance with a state of a worker in the workspace, the ion generator comprising:

an ion generation unit configured to generate the ions;

an acquisition unit configured to acquire, as the state of the worker, worker information related to at least one of drowsiness of the worker and a state of work of the worker, wherein the worker information includes a contact state with an object touched by the worker to perform work; and an ion generation control unit configured to control, based on the worker information, an emission amount of the ions per unit time, wherein the ion generation control unit is configured to increase the emission amount of the ions per unit time in a case that the contact state does not satisfy a predetermined condition.

2. The ion generator according to claim 1, wherein the worker information indicates a degree of drowsiness of the worker, the degree of drowsiness of the worker is identified based on at least one of an image of a face of the worker obtained by imaging the worker during the work, biological information of the worker during the work, and movement information indicating a change in movement of the worker during the work, and the ion generation control unit is configured to increase the emission amount of the ions per unit time as the degree of drowsiness of the worker increases.

3. The ion generator according to claim 1, further comprising:

an air sending unit configured to generate an airflow for sending the ions generated by the ion generation unit to outside, wherein the ion generation control unit is configured to control the emission amount of the ions per unit time by controlling an airflow rate of the air sending unit while the ions are being emitted.

4. An ion generator configured to emit air containing ions into a workspace in accordance with a state of a worker in the workspace, the ion generator comprising:

an ion generation unit configured to generate the ions;

an acquisition unit configured to acquire, as the state of the worker, worker information related to at least one of drowsiness of the worker and a state of work of the worker;

an ion generation control unit configured to control, based on the worker information, an emission amount of the ions per unit time;

an air sending unit configured to generate an airflow for sending the ions generated by the ion generation unit to the outside, a louver configured to change an air direction of the air containing the ions;

a detection unit configured to detect a direction of the worker relative to the ion generator; and an air direction switching unit configured to cause the louver to change the air direction based on the direction of the worker detected by the detection unit.

5. An ion generator configured to emit air containing ions into a workspace in accordance with a state of a worker in the workspace, the ion generator comprising:

an ion generation unit configured to generate the ions;

an acquisition unit configured to acquire, as the state of the worker, worker information related to at least one of drowsiness of the worker and a state of work of the worker;

an ion generation control unit configured to control, based on the worker information, an emission amount of the ions per unit time; and a notification unit, wherein the ion generation control unit, when changing the emission amount of the ions per unit time, causes the notification unit to provide a notification of the state of the worker based on the worker information and information indicating a change in the emission amount of the ions per unit time.

* * * * *